US009460901B2

United States Patent
Kawase

(10) Patent No.: US 9,460,901 B2
(45) Date of Patent: Oct. 4, 2016

(54) DATA-PROCESSING SYSTEM FOR CHROMATOGRAPH MASS SPECTROMETRY

(71) Applicant: SHIMADZU CORPORATION, Kyoto-shi, Kyoto (JP)

(72) Inventor: Tomohiro Kawase, Kyoto (JP)

(73) Assignee: SHIMADZU CORPORATION, Kyoto-shi (JP)

( * ) Notice: Subject to any disclaimer, the term of this patent is extended or adjusted under 35 U.S.C. 154(b) by 672 days.

(21) Appl. No.: 13/869,673

(22) Filed: Apr. 24, 2013

(65) Prior Publication Data

US 2013/0289893 A1    Oct. 31, 2013

(30) Foreign Application Priority Data

Apr. 26, 2012 (JP) ................. 2012-100886

(51) Int. Cl.
| | |
|---|---|
| *G01N 31/00* | (2006.01) |
| *H01J 49/00* | (2006.01) |
| *G01N 30/86* | (2006.01) |
| *H01J 49/42* | (2006.01) |

(52) U.S. Cl.
CPC ....... *H01J 49/0036* (2013.01); *G01N 30/8679* (2013.01); *H01J 49/4215* (2013.01)

(58) Field of Classification Search
CPC ............... G01N 30/7206; G01N 30/8682; H01J 49/0422; H01J 49/0036; H01J 49/004
USPC ................................... 702/22–25
See application file for complete search history.

(56) References Cited

U.S. PATENT DOCUMENTS 8,134,121 B2 * 3/2012 Miyagawa ............ 250/282
9,209,004 B2 * 12/2015 Yamada

FOREIGN PATENT DOCUMENTS

| CN | 101384898 A | 3/2009 |
|---|---|---|
| CN | 101558568 A | 10/2009 |
| JP | 2011-249109 | 12/2011 |

OTHER PUBLICATIONS

Examination Report Received for Chinese Patent Application No. 201310150866.6, mailed on Apr. 28, 2015, 7 pages. (1 page of English Translation and 6 pages of Official Copy).

(Continued)

*Primary Examiner* — An Do
(74) *Attorney, Agent, or Firm* — Morgan, Lewis & Bockius LLP

(57) ABSTRACT

In processing chromatographic data, collected by performing a measurement for each of the segments which respectively define time ranges, a system determines whether there is any boundary sandwiched between two temporally continuous segments whose measurement modes are the same and which has the same m/z value designated by an operator to be displayed. If such a boundary exists, the measurement mode common to the two neighboring segments across that boundary is identified, and the system determines whether the parameter values corresponding to that measurement mode are the same. If they are the same, the partial chromatograms corresponding to the two segments show a temporal change in the intensity of the same kind of ion. Accordingly, the two neighboring measurement points across the boundary are connected by interpolation to create a chromatogram with no missing portion.

9 Claims, 4 Drawing Sheets

(56) References Cited

OTHER PUBLICATIONS

Qing et al., Base Structure Improvement and New Search Algorithm of an Organic Mass Analysis Spectrum, Chinese Journal of Analytical Chemistry (Fenxi Huexue), vol. 34, No. 7, Jul. 2006, p. 1049. (In accordance with 37 CFR § 1.98(a) (3)).

Examination Report received for Chinese Patent Application No. 201310150866.6, mailed on Aug. 5, 2014, 6 pages (1 page of English Translation and 5 pages of Official Copy).

* cited by examiner

Fig. 3A

| MODE | SEGMENT #1 | | SEGMENT #2 | |
|---|---|---|---|---|
| | Q1 - m/z | Q3 - m/z | Q1 - m/z | Q3 - m/z |
| MRM | (EVENT #1) 300<br>(EVENT #2) 200 | (EVENT #1) 200<br>(EVENT #2) 100 | (EVENT #1) 300<br>(EVENT #2) 300 | (EVENT #1) 150<br>(EVENT #2) 200 |
| Q1 SIM | (EVENT #1) 100<br>(EVENT #2) 200<br>(EVENT #3) 300 | / | (EVENT #1) 150<br>(EVENT #2) 300<br>(EVENT #3) 200 | / |
| Q3 SIM | / | (EVENT #1) 100<br>(EVENT #2) 200 | / | (EVENT #1) 200<br>(EVENT #2) 150 |

CONNECTING PROCESS ⇩ BOUNDARY(t2)

Fig. 3B

| MODE | SEGMENT #1 TIME t1~t2 | | SEGMENT #2 TIME t2~t3 | | CONNECTING PROCESS |
|---|---|---|---|---|---|
| | Q1 - m/z | Q3 - m/z | Q1 - m/z | Q3 - m/z | |
| MRM | (EVENT #1) 300<br>(EVENT #2) 200 | (EVENT #1) 200<br>(EVENT #2) 100 | (EVENT #1) 300<br>(EVENT #2) 200 | (EVENT #1) 150<br>(EVENT #2) 200 | CONNECT CHROMATOGRAMS OF Q1:300 AND Q3:200 |
| Q1 SIM | (EVENT #1) 100<br>(EVENT #2) 200<br>(EVENT #3) 300 | | (EVENT #1) 150<br>(EVENT #2) 300<br>(EVENT #3) 200 | | CONNECT CHROMATOGRAMS OF m/z 300 AND m/z 200, RESPECTIVELY |
| Q3 SIM | | (EVENT #1) 100<br>(EVENT #2) 200 | | (EVENT #1) 200<br>(EVENT #2) 150 | CONNECT ONLY CHROMATOGRAMS OF m/z 200 |

WITHOUT CONNECTING PROCESS

WITH CONNECTING PROCESS

DATA-PROCESSING SYSTEM FOR CHROMATOGRAPH MASS SPECTROMETRY

TECHNICAL FIELD

The present invention relates to a system for processing data collected by a chromatograph mass spectrometer including a chromatograph, such as a gas chromatograph (GC) or liquid chromatograph (LC), combined with a quadrupole mass spectrometer, and particularly to a data-processing system suitable for processing data collected by a chromatograph tandem quadrupole mass spectrometer including a chromatograph combined with a tandem quadrupole mass spectrometer (which may also be called a "triple quadrupole mass spectrometer").

BACKGROUND ART

A method called an MS/MS analysis (or tandem analysis) is widely used as one of the mass spectrometric techniques for identification, structural analyses or quantitative determination of compounds having large molecular weights. There are various kinds of mass spectrometers with different configurations designed for the MS/MS analysis, among which tandem quadrupole mass spectrometers are characterized by their relatively simple structure as well as easy operation and handling.

In a generally used tandem quadrupole mass spectrometer, ions generated from a sample in an ion source are introduced into a first quadrupole mass filter (which is often represented as "Q1"), in which an ion having a specific mass-to-charge ratio (m/z) is selected as a precursor ion. This precursor ion is introduced into a collision cell containing an ion guide with four or more poles (this ion guide is commonly represented as "q2"). A collision-induced dissociation (CID) gas, such as argon, is supplied to this collision cell, and the precursor ion in the collision cell collides with this CID gas, to be fragmented into various kinds of product ions. These product ions are introduced into a second quadrupole mass filter (which is often represented as "Q3"), which selectively allows a product ion having a specific mass-to-charge ratio (m/z) to pass through it and reach a detector, to be thereby detected.

The tandem quadrupole mass spectrometer can be used independently. However, this device is often coupled with a chromatograph, such as a gas chromatograph (GC) or liquid chromatograph (LC). In recent years, chromatograph tandem quadrupole mass spectrometers have become vital devices in the field of analyzing a trace amount of sample containing a large amount of compounds or contaminated with various impurities, such as testing residual pesticides in foodstuffs, testing environmental pollutants, checking the concentration of medicinal chemicals in blood, or screening drugs or poisonous substances.

MS/MS analyses by chromatograph tandem quadrupole mass spectrometers can be conducted in various measurement modes, such as a multiple reaction monitoring (MRM) mode, precursor-ion scan mode, product-ion scan mode, and neutral-loss scan mode (see Patent Document 1). In the MRM mode, the mass-to-charge ratio at which ions are allowed to pass through is fixed in each of the first and second quadrupole mass filters so as to fragment a specific kind of precursor ion and measure an intensity (or amount) of a specific kind of product ion resulting from the fragmentation. The two-stage mass filtering in the MRM measurement eliminates unwanted components other than those to be analyzed, ions originating from impurities, and neutral particles, so that an ion intensity signal with high signal-to-noise ratio can be obtained. Due to this feature, the MRM measurement is particularly effective for the quantitative analysis of a trace amount of component. For example, gas chromatograph tandem mass spectrometers (GC/MS/MS) are frequently operated in the MRM mode to perform a simultaneous multi-component quantitative analysis of residual pesticides, which requires determining the quantity of an extremely small amount of components.

The chromatograph tandem mass spectrometer can also be operated similarly to a chromatograph mass spectrometer having only one quadrupole mass filter to perform a scan measurement or selected ion monitoring (SIM) measurement, neither of which involves the dissociation of ions. For example, it can be operated in a Q1SIM mode or Q1 scan mode, in which case the ion selection is performed in the first quadrupole mass filter while ions are allowed to pass through the second quadrupole mass filter, as well as in a Q3SIM mode or Q3 scan mode, in which case all the ions are initially allowed to pass through the first quadrupole mass filter, and subsequently, undergo the selection process by the second quadrupole mass filter. A Q3SIM mode is frequently used for a quantitative analysis of known kinds of compounds which have a relatively low molecular weight and are less likely to yield characteristic product ions.

In a chromatograph quadrupole mass spectrometer or a tandem version of the same device, various components in a sample are temporally separated in the chromatograph. However, if the sample contains too many compounds of interest, the chromatograph cannot adequately separate them, allowing two or more compounds to overlap each other and be introduced into the mass spectrometer in almost the same range of time. To address this problem, this type of mass spectrometer conventionally has the capability of alternately performing Q3SIM and MRM measurements for multiple ions of different mass-to-charge ratios within the same range of time to obtain an ion-intensity signal originating from each of the different compounds.

For convenience of user setting of the measurement conditions of such a complex measurement, the following method has been adopted in the conventional chromatograph quadrupole mass spectrometer:

Each measurement mode to be performed and the measurement conditions for that measurement mode (e.g. for the MRM mode, the conditions include the m/z values to be selected by the first quadrupole mass filter and the m/z values to be selected by the second quadrupole mass filter) are specified as "events." If a plurality of events are specified for a certain range of time, a set of analyses are sequentially and cyclically repeated, with each analysis being conducted according to the conditions specified in one of the plurality of events. In the case of a quantitative analysis by an SIM or MRM measurement, each event basically corresponds to one of the compounds to be analyzed, because the content of each event is determined so as to analyze an ion or ions having mass-to-charge ratios characteristic of the target compound.

In this method, since a plurality of measurements are sequentially performed according to the events, setting a larger number of events to the same range of time leads to a shorter period of time assigned to each measurement or a longer interval of time for the repetition of the same event. In the former case, the accuracy and sensitivity of the measurement will deteriorate, which leads to a decrease in the accuracy of the quantitative determination. The latter case has the possibility of overlooking a maximum value of the component concentration, i.e. a peak top on the chromatogram, which deteriorates the accuracy of the peak area and similarly leads to a decrease in the accuracy of the quantitative determination. To avoid these situations, the range of time from the beginning (sample injection) to the end of the analysis is divided into a plurality of time units called "segments", or a plurality of segments which do not overlap each other are set within the range of time from the beginning to the end of the analysis, and the events are set for each segment.

FIG. 5 is a chart showing the concept of setting segments and events with respect to the elapse of time. The segments may be specified continuously (as in the case of segments #1 through #3 in the figure) or discontinuously (as in the case of segments #3 and #4) on the time axis. In most cases, users choose the continuous setting of the segments. Each segment has one or more events allotted thereto. For example, during the period of time from t1 to t2, for which segment #1 is set, two measurements according to the two events, i.e. events #1 and #2, will be repeated. By this method, for each compound to be analyzed, users only need to specify the events for the quantitative determination in one or more segments around the retention time of the compound in question. It is unnecessary to allot many events to each and every event.

As already explained, in the case of using events and segments to set measurement conditions, allotting a smaller number of events to one segment provides a higher accuracy of the chromatogram. The reduction of the number of events can be achieved by decreasing the time span of the segments and setting the segments at smaller intervals in accordance with the retention times of the compounds to be analyzed. However, it is often the case that a compound to be analyzed appears at a point in time displaced from the expected retention time due to a change in the condition of the chromatographic separation or other factors. Therefore, if the time span of the segments is reduced, a peak which characterizes the target compound on the chromatogram will probably appear across the boundary of the segments, without being included in one segment.

In conventional devices, in the case where a chromatogram peak lies across the boundary of two or more segments, if the same measurement mode with the same measurement conditions is allotted to the same event number in any of these segments, the obtained partial chromatograms can be connected across the segments to draw a continuous peak curve. However, even when the mode and conditions of the measurements are the same, if the event number is different, the resultant chromatogram will have a missing portion at the boundary of the segments, as shown in FIG. 4A. Consequently, for a chromatogram with a peak lying on two or more segments, it is impossible to correctly perform the peak-waveform processing and determine the correct peak area. Such a situation often results in a significant deterioration in the reliability of the quantitative determination or an unsuccessful identification of a component.

To avoid such a situation, analysis operators (users) need to determine whether the leading or tailing portion of a peak is likely to appear across the boundary of the segments, and if this situation is expected, they need to appropriately arrange the condition setting so that all the events with the same measurement mode and the same measurement conditions will have the same event number. This task is cumbersome and puts a heavy workload on the operators. Furthermore, such a task is likely to cause users to make some mistakes, thus constituting a major cause of an incorrect result of the analysis.

BACKGROUND ART DOCUMENT

Patent Document

Patent Document 1: JP-A 2011-249109

SUMMARY OF THE INVENTION

Problem to be Solved by the Invention

The present invention has been developed to solve the previously described problem. Its objective is to provide a data-processing system for chromatographic mass spectrometry capable of determining a continuous peak curve on a chromatogram and performing an appropriate peak-waveform processing, component identification and other types of data processing, even if the concerned peak is spread across a boundary of the segments appropriately defined on the time axis, regardless of what event numbers are set in each of the two segments neighboring each other across the boundary.

Means for Solving the Problems

The present invention aimed at solving the aforementioned problem is a data-processing system for chromatographic mass spectrometry for creating a chromatogram by processing data repeatedly collected by a chromatograph quadrupole mass spectrometer capable of setting a mass spectrometric measurement condition for each of the segments corresponding to a plurality of time ranges continuously or discontinuously set on a time axis, including:

a) a memory for storing a parameter value specified as a mass spectrometric measurement condition for each of the segments;

b) a determiner for retrieving, from the memory, a predetermined parameter value for each of a pair of continuously located segments, and for determining whether the retrieved parameter values are identical; and c) a chromatogram creation processor for creating a chromatogram by connecting partial chromatograms based on the data collected for each of the aforementioned pair of segments under the corresponding measurement condition, when the determiner has determined that the retrieved parameter values are identical.

The chromatogram created by the chromatogram creation processor can be presented on a screen of a display unit. It may also be subjected to a data processing for computing a peak area or determining the location (point in time) of a peak top.

The aforementioned chromatograph quadrupole mass spectrometer is either a chromatograph quadrupole mass spectrometer with a single quadrupole mass filter or a chromatograph tandem quadrupole mass spectrometer with two tandem-arranged quadrupole mass filters separated by a collision cell. The chromatograph is either a gas chromatograph or a liquid chromatograph.

In the data-processing system for chromatographic mass spectrometry according to the present invention, the chromatogram is, for example, a mass chromatogram, which represents a temporal change in the intensity of an ion having a specific mass-to-charge ratio, or a total ion chromatogram, which represents a temporal change in the sum of the intensities of the ions over the entire range of mass-to-charge ratios (more exactly, the range of mass-to-charge ratios covered by a mass scan).

In the data-processing system for chromatographic mass spectrometry according to the present invention, for example, when a plurality of segments or time ranges have been specified and a command for creating a chromatogram is given, the determiner examines the specified segments to determine, for each pair of the neighboring segments, whether or not the two segments are temporally continuous, and retrieves, from the memory, a predetermined parameter value for each of the two segments if these segments have been found to be continuous. Then, it determines whether or not the retrieved parameter values corresponding to the two segments are identical.

If the retrieved parameter values are not identical, the two partial chromatograms respectively created from the data collected at the two corresponding segments are most likely to be unrelated to each other even if these segments are temporally continuous. Conversely, if the retrieved parameter values are identical, it is possible to determine that the partial chromatograms corresponding to the two segments should form a continuous chromatogram, as in the case of two mass chromatograms obtained at the same mass-to-charge ratio. Accordingly, if the retrieved parameter values have been found to be identical, the chromatogram creation processor connects the partial chromatograms corresponding the two segments at that boundary to create a chromatogram. Thus, even if there is a peak on the chromatogram corresponding to a target compound lying across the boundary of two segments, a continuous curve extending from the beginning to the end of that peak is obtained, and a waveform processing of the peak or the component identification based on the retention time can be correctly performed. When presented on a display screen, the resultant chromatogram has no missing portion in the peak curve, thus allowing operators to visually and securely check the chromatogram.

As already stated, the chromatograph tandem quadrupole mass spectrometer can perform mass spectrometry in various measurement modes, including the MRM mode. The chromatograph quadrupole mass spectrometer with a single quadrupole mass filter can normally perform mass spectrometry in two measurement modes: the SIM mode and the scan mode.

Accordingly, in a preferable mode of the data-processing system for chromatographic mass spectrometry according to the present invention, the memory holds a measurement mode and a parameter value specified as the mass-spectrometric measurement conditions for each of the segments, the determiner determines whether the measurement modes and the predetermined parameter values for the aforementioned two segments are identical, and the chromatogram creation processor connects the partial chromatograms if the measurement modes are the same and the parameter values are also the same.

In another preferable mode of the present invention, the data-processing system for chromatographic mass spectrometry further includes a specifying section for allowing an operator to specify a mass-to-charge ratio, a range of mass-to-charge ratios or a target compound for which a chromatogram needs to be displayed, wherein:

the determiner determines whether the displayed mass-to-charge ratios, ranges of mass-to-charge ratio or target compounds specified for the aforementioned two segments through the specifying section are identical as well as whether the predetermined parameter values corresponding to the aforementioned two segments are identical; and the chromatogram creation processor connects the partial chromatograms if the parameter values are identical and the displayed mass-to-charge ratios, ranges of mass-to-charge ratio or target compounds are also identical.

With this configuration, even if a chromatogram peak corresponding to a target compound to which the operator is paying attention lies across two or more segments, the chromatograph peak corresponding to that compound will be displayed from the beginning to the end thereof without any missing portion.

In the data-processing system for chromatographic mass spectrometry according to the present invention, the predetermined parameter value on which the identification determination is made by the determiner is a parameter dependent on the mass-spectrometric measurement mode.

Specifically, if the chromatograph quadrupole mass spectrometer is a chromatograph tandem quadrupole mass spectrometer, the aforementioned parameter value may be the value of the mass-to-charge ratio of an ion selected by one of the two quadrupole mass filters in one of the following modes: a Q1SIM mode, in which an ion is selected according to the mass-to-charge ratio thereof by the first quadrupole mass filter, while neither ion dissociation in the collision cell nor ion selection by the second quadrupole mass filter is performed; a Q3SIM mode, in which neither ion selection by the first quadrupole mass filter nor ion dissociation in the collision cell is performed, while an ion is selected according to the mass-to-charge ratio thereof by the second quadrupole mass filter; and an MRM mode, in which an ion is selected according to the mass-to-charge ratio thereof by the first quadrupole mass filter, the selected ion is dissociated in the collision cell, and a product ion created by dissociation is selected according to the mass-to-charge ratio thereof by the second mass spectrometer.

Furthermore, if the chromatograph quadrupole mass spectrometer is constructed as a chromatograph tandem quadrupole mass spectrometer, the aforementioned parameter value may be the value of the mass-to-charge ratio of an ion to be selected by the second quadrupole mass filter in a precursor-ion scan mode, or the value of the mass-to-charge ratio of an ion to be selected by the first quadrupole mass filter in a product-ion scan mode. The aforementioned parameter value may otherwise be the value of a neutral loss corresponding to the difference between the mass-to-charge ratio of an ion selected by the first quadrupole mass filter and the mass-to-charge ratio of an ion selected by the second quadrupole mass filter in a neutral-loss scan mode.

In the case of a measurement mode including a mass scan of a predetermined range of mass-to-charge ratios by a quadrupole mass spectrometer in the aforementioned manner (e.g. as in the precursor-ion scan mode, the product-ion scan mode or the neutral-loss scan mode in a chromatograph tandem quadrupole mass spectrometer), the predetermined parameter value may be a range of mass-to-charge ratios to be scanned, i.e. the value of the mass-to-charge ratio at which the mass scan begins and the value of the mass-to-charge ratio at which the mass scan ends.

If the quadrupole mass spectrometer is not a tandem type but a device with a single quadrupole mass filter, the predetermined parameter value may be the value of a range of mass-to-charge ratios in the scan mode or the value of the mass-to-charge ratio in the SIM mode.

Effect of the Invention

In the data-processing system for chromatographic mass spectrometry according to the present invention, even if a chromatogram (e.g. a mass chromatogram or total ion mass chromatogram) has a peak that is not included in one segment but lies across two or more segments, it is possible to create a chromatogram with no missing portion at the boundary of the segments as long as a predetermined measurement parameter has the same value for all of those two or more segments. Any chromatogram peak corresponding to one compound to be analyzed forms a complete curve from the beginning to the end thereof with no missing portion, so that a waveform processing (e.g. the calculation of a peak area for a quantitative analysis) can be correctly performed. Furthermore, since the location of the peak top can be correctly determined by the waveform processing, the component identification using the retention time can also be correctly performed. When presented on a display screen, the chromatogram will have a natural form and will not seem strange to viewers.

BRIEF DESCRIPTION OF THE DRAWINGS

FIGS. 3A and 3B illustrates the chromatogram connection process in the GC/MS/MS of the present embodiment.

BEST MODE FOR CARRYING OUT THE INVENTION

One embodiment of the gas chromatograph tandem quadrupole mass spectrometer (GC/MS/MS) provided with a data-processing system for chromatographic mass spectrometry according to the present invention is hereinafter described in detail with reference to the attached drawings.

Figure 1:
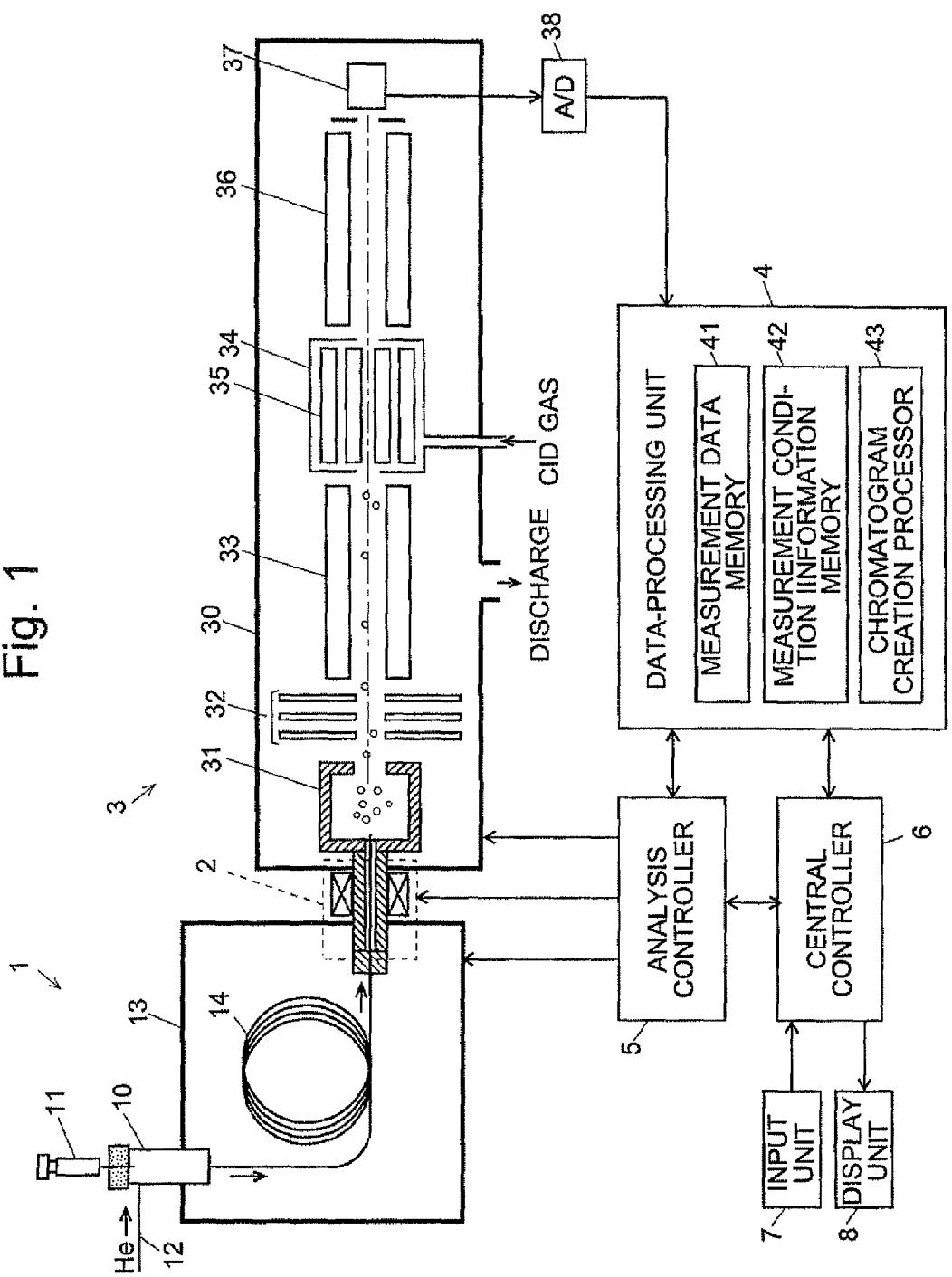
FIG. 1 shows a schematic configuration of one embodiment of a GC/MS/MS having a data-processing system for chromatographic mass spectrometry according to the present invention.

FIG. 1 is a schematic configuration diagram of the GC/MS/MS according to the present embodiment. In a gas chromatograph (GC) unit 1, a sample vaporization chamber 10 is provided at the inlet of a column 14, which is heated to an appropriate temperature by a column oven 13. A carrier gas 12 is supplied through a carrier-gas passage 12 to the sample vaporization chamber 10 at a predetermined flow rate and introduced into the column 14. In this state, when a trace amount of liquid sample is injected from a micro syringe 11 into the sample vaporization chamber 10, the liquid sample instantly vaporizes and is carried into the column 14 by the carrier-gas flow. While passing through the column 14, the sample gas is temporally separated into various compounds before arriving at the outlet of the column 14. After exiting the column 14, these compounds pass through the interface unit 2 including a heater and other elements, to be introduced into an ionization chamber 31 provided in a vacuum chamber 30 in a mass spectrometer (MS) unit 3.

The molecules of the compounds introduced into the ionization chamber 31 are ionized by an appropriate method, such as electron ionization (EI) or chemical ionization (CI). The produced ions are drawn to the outside of the ionization chamber 31 and converged by an ion lens 32, to be introduced into a space extending along the axis of a first quadrupole mass filter (Q1) 33, which consists of four rod electrodes. A voltage produced by superposing a DC voltage on an AC voltage is applied from a power source (not shown) to the first quadrupole mass filter 33, where only a specific kind of ion whose mass-to-charge ratio corresponds to the applied voltage is allowed to pass through the first quadrupole mass filter 33 in the axial direction thereof; to be introduced into a collision cell 34.

The collision cell 34 contains a multipole ion guide (q2) 35 for converging ions by the effect of a radio-frequency electric field. A collision-induced dissociation (CID) gas, such as argon gas, is continuously or intermittently introduced from the outside into the collision cell 34. The ions introduced into the collision cell 34 come in contact with the CID gas, to be fragmented into product ions. While being converged, the resultant fragment ions are introduced into a space extending along the axis of a second quadrupole mass filter (Q3) 36. Similar to the first quadrupole mass filter 33, the second quadrupole mass filter 36 consists of four rod electrodes. A voltage produced by superposing a DC voltage on an AC voltage is applied from a power source (not shown) to those rod electrodes. Only a specific kind of product ion whose mass-to-charge ratio corresponds to the applied voltage is allowed to pass through the second quadrupole mass filter 33 in the axial direction thereof and reach an ion detector 37.

The detection signal produced by the ion detector 37 is converted into digital data by an analogue-to-digital (A/D) converter 38 and sent to a data-processing unit 4. The data-processing unit 4 includes a measurement data memory 41, a measurement condition information memory 42, a chromatogram creation processor 43 and other functional blocks to perform a process characteristic of the present invention. The operations of the DC unit 1, the interface unit 2 and the components included in the MS unit 3 are individually controlled by an analysis controller 5. A central controller 6, to which an input unit 7 (including a keyboard and a mouse or similar pointing device) and a display unit 8 are connected, is responsible for controlling input/output operations as well as basic system operations at higher levels than the analysis controller 5. The data-processing unit 4, the analysis controller 5 and the central controller 6 can be embodied by using a personal computer as the hardware resource and executing a preinstalled, dedicated controlling-and-processing software program on that personal computer.

The MS unit 3 of this GC/MS/MS can perform various modes of measurements. For example, the MRM mode, the precursor-ion scan mode, the product-ion scan mode or the neutral-loss scan mode can be used as a measurement mode for an MS/MS analysis, which involves a CID operation performed in the collision cell 34. For an analysis with no CID operation performed in the collision cell 34, the Q1SIM mode, the Q3SIM mode, the Q1 scan mode and the Q3 scan mode are available.

A measurement operation in the GC/MS/MS according to the present embodiment, i.e. the operation of collecting mass spectrometric data, is hereinafter described.

Figure 5:
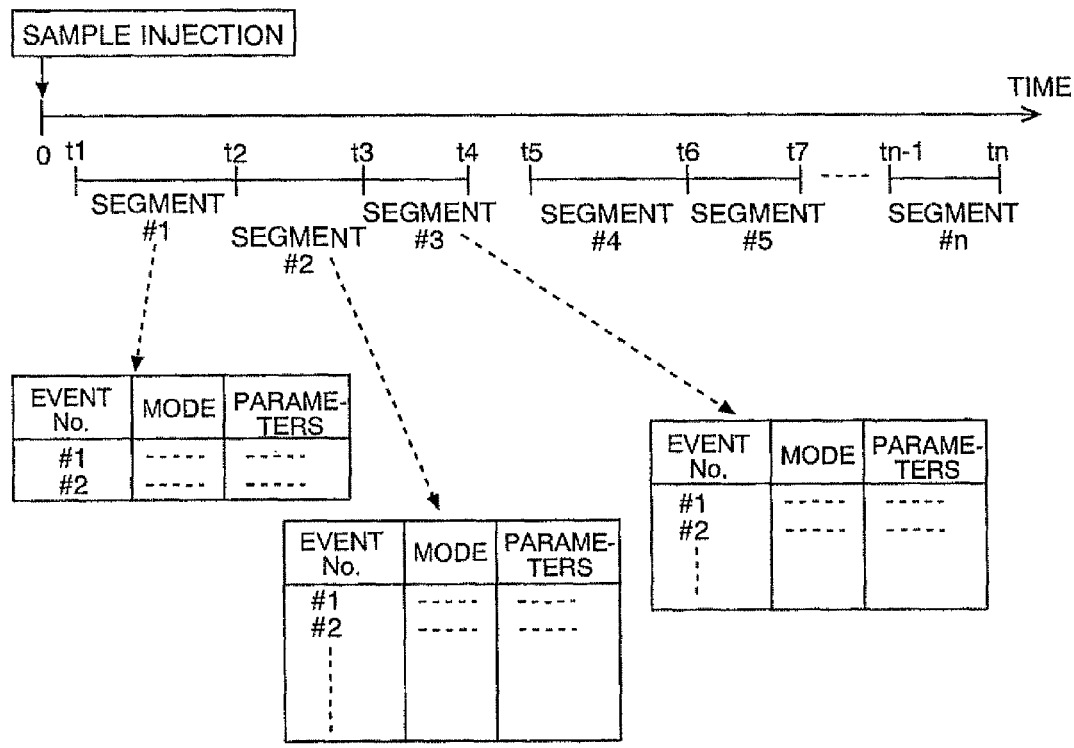
FIG. 5 shows the concept of setting segments and events with respect to the elapse of time in a conventional chromatograph tandem quadrupole mass spectrometer.

Prior to the measurement of a sample of interest, an operator sets the measurement conditions and other items of information through the input unit 7 as follows: Initially, as shown in FIG. 5, segments are appropriately defined over the entire range of time from the start point of the analysis (the point of sample injection) to the point in time at which the measurements for all the target compounds are completed. In the case of a quantitative analysis of known kinds of compounds, the retention time of each compound is known beforehand, so that the segments should normally be defined in such a manner that the smallest possible number of compounds will appear in each segment. For each of these segments, the operator specifies the measurement mode to be performed in that segment as well as various parameter values required for that measurement mode. The thus specified measurement mode and parameter values constitute one "event." Each event is given an identification number. As already noted, two or more events can be specified for one segment.

One example of the parameter values included in each event is hereinafter described. As shown in FIG. 3A, in the case of the MRM mode, the mass-to-charge ratio to be selected by the first quadrupole mass filter 33 (Q1-m/z) and the mass-to-charge ratio to be selected by the second quadrupole mass filter 36 (Q3-m/z) are included in the parameter values. In the case of the Q1 SIM mode, the mass-to-charge ratio to be selected by the first quadrupole mass filter 33 (Q1-m/z) is included in the parameter values. In the case of the Q3 SIM mode, the mass-to-charge ratio to be selected by the second quadrupole mass filter 36 (Q3-m/z) is included in the parameter values. Though not shown in FIG. 3A, for a measurement mode in which a mass scan is performed in one or both of the quadrupole mass filters 33 and 36 (e.g. as in the precursor-ion scan mode), the starting and ending mass-to-charge ratios of the mass scan will be included in the parameter values. In this case, the scan speed may also be included in the parameter values.

The information about the segments and events specified by the operator are held in a memory (not shown) inside the central controller 6 as well as stored in a measurement condition information memory 42 of the data-processing unit 4. Subsequently, when the operator enters a command for executing the measurement through the input unit 7, a corresponding instruction is given through the central controller 6 to the analysis controller 5, whereupon the GC unit 1, the interface unit 2 and the MS unit 3 begin respective operations to perform a measurement under the control of the analysis controller 5. That is to say, in the GC unit 1, a target sample is dropped into the sample vaporization chamber 10. The vaporized sample is carried into the column 14 by the carrier-gas flow. With the point of injection of the sample as the starting point, the MS unit 3 measures the elapsed time, and during each period of time specified as a segment, it repeatedly performs a measurement according to one or more events set for that segment.

For example, if two events #1 and #2 corresponding to the MRM mode in FIG. 3A are set for two segments #1 and #2, an MRM measurement according to event #1 (for selecting a precursor ion of m/z 300 and a product ion of m/z 200) and an MRM measurement according to event #2 (for selecting a precursor ion of m/z 200 and a product ion of m/z 100) are alternately repeated, during the period of time from t1 to t2 (segment #1), and an ion intensity is detected by the ion detector 37 in each of the two MRM measurements. After the point in time t2, i.e. the boundary between the two segments #1 and #2, the next segment #2 covering the period of time from t2 to t3 begins, during which an MRM measurement according to event #1 (for selecting a precursor ion of m/z 300 and a product ion of m/z 150) and an MRM measurement according to event #2 (for selecting a precursor ion of m/z 300 and a product ion of m/z 200) are alternately repeated, and an ion intensity is detected by the ion detector 37 in each of the two MRM measurements.

In this manner, various measurements are performed according to the specified segments and events until the entire measurement process is completed. During this process, the ion intensities obtained by the ion detector 37 are converted into digital data and stored in the measurement data memory 41.

Figure 2:
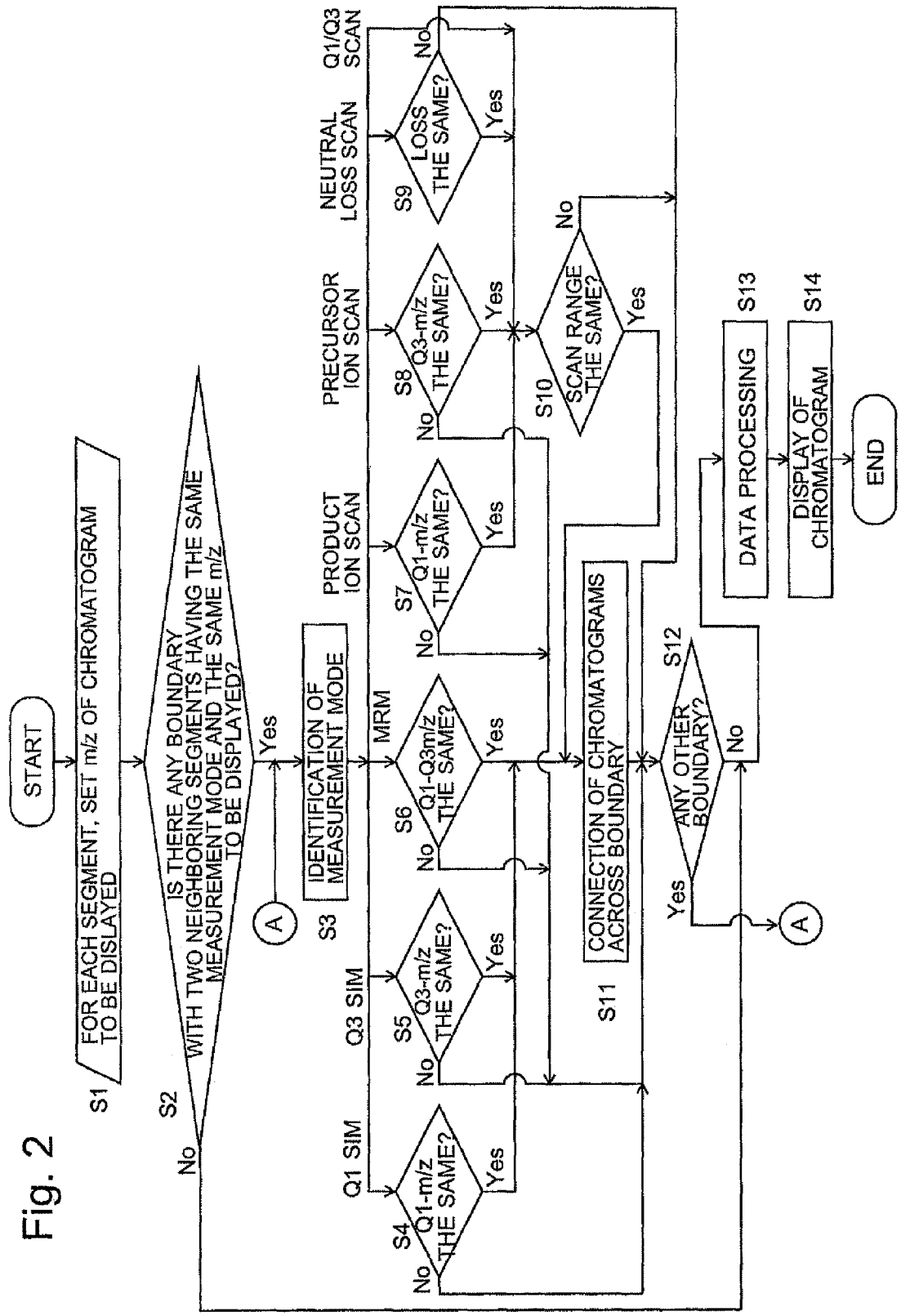
FIG. 2 shows a flowchart of a chromatogram connection process in the GC/MS/MS of the present embodiment.
Figure 4A:
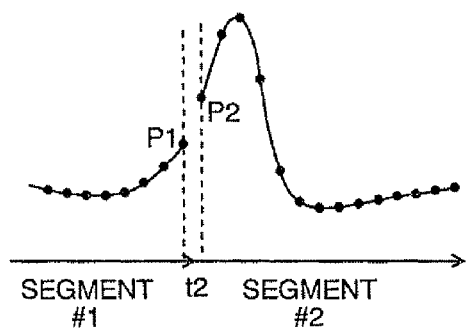
FIGS. 4A and 4B respectively show one example of the chromatogram before and after the chromatogram connection process in the GC/MS/MS of the present embodiment.
Figure 4B:
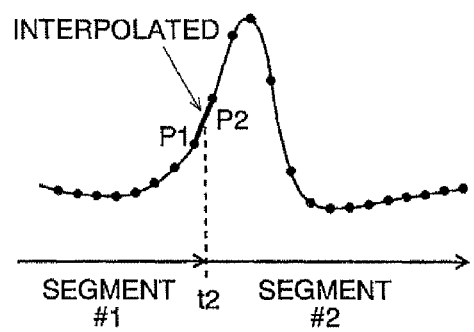

A chromatogram creation process including a chromatogram connection process characteristic of the present embodiment is hereinafter described with reference to the flowchart shown in FIG. 2. The following process is performed under the condition that mass spectrometric data as previously described have been stored in the measurement data memory 41, and the measurement conditions (events) under which the spectrometric measurements were performed are stored in the measurement condition information memory 42.

Initially, by using the input unit 7, an analysis operator specifies, for each segment, the type of chromatogram to be presented on the screen of the display unit 8 as well as one or more m/z values (Step S1). In the present example, specifying the type of chromatogram means selecting either the mass chromatogram or the total ion chromatogram. When the mass chromatogram of a specific mass-to-charge ratio obtained by a measurement in either the Q1 SIM or Q3 SIM mode is to be displayed, the mass-to-charge ratio of interest should be specified. When a mass chromatogram obtained by an MRM measurement for a specific kind of precursor ion and a specific kind of product ion is to be displayed, the m/z value of the precursor ion and that of the product ion should be specified. When a total ion chromatogram obtained by summing the ion intensities on the mass spectrum obtained by a measurement in either the product-ion scan mode or precursor-ion scan mode is to be displayed, the m/z values corresponding to the starting and ending points of the mass scan of the precursor ion or product ion should be specified. When a total ion chromatogram obtained by summing the ion intensities on the mass spectrum obtained by a measurement in the neutral-loss scan mode is to be displayed, the m/z values corresponding to the starting and ending points of the mass scan in the first quadrupole mass filter 33 should be specified. When a total ion chromatogram obtained by summing the ion intensities on the mass spectrum obtained by a measurement in either the Q1 or Q3 scan mode is to be displayed, the m/z values corresponding to the starting and ending points of the mass scan in either the first quadrupole mass filter 33 or the second quadrupole mass filter 36 should be specified.

After the m/z values and other information are set in Step S1, the chromatogram creation processor 43 retrieves a set of information relating to the segments designated for the chromatogram display and the corresponding events from the measurement condition information memory 42. Then, it determines 1) whether the designated segments are temporally continuous, 2) whether the events specified for those continuous (neighboring) segments include any common measurement mode, and 3) whether the continuous segments have the same m/z value specified in Step S1 as the mass-to-charge ratio to be displayed (Step S2). If there is no boundary between two segments which are continuous and satisfy the aforementioned conditions, it is unnecessary to perform the chromatogram connection process as will be described later, so that the operation proceeds to Step S13.

In Step S2, if it has been found that there is at least one boundary which satisfies the aforementioned conditions, it is determined what is the common measurement mode specified for both segments neighboring each other at the boundary (Step S3). Then, depending on the result of Step S3, the operation proceeds to one of Steps S4-S10. That is to say, if the common measurement mode is identified as the Q1SIM mode, it is determined whether any two events respectively set for the two segments neighboring each other across the aforementioned boundary have the same value specified as the mass-to-charge ratio to be selected by the first quadrupole mass filter 33 (Step S4). If the common measurement mode has been identified as the Q3SIM mode, it is determined whether any two events respectively set for the two segments neighboring each other across the aforementioned boundary have the same value specified as the mass-to-charge ratio to be selected by the second quadrupole mass filter 36 (Step S5). If the common measurement mode has been identified as the MRM mode, it is determined whether any two events respectively set for the two segments neighboring each other across the aforementioned boundary have the same values specified as the mass-to-charge ratios to be respectively selected by the first and second quadrupole mass filters 33 and 36 (Step S6).

If the common measurement mode has been identified as the product-ion scan mode, it is determined whether any two events respectively set for the two segments neighboring each other across the aforementioned boundary have the same value specified as the mass-to-charge ratio to be selected by the first quadrupole mass filter 33 (Step S7). If the common measurement mode has been identified as the precursor-ion scan mode, it is determined whether any two events respectively set for the two segments neighboring each other across the aforementioned boundary have the same value specified as the mass-to-charge ratio to be selected by the second quadrupole mass filter 36 (Step S8). If the common measurement mode has been identified as the neutral-loss scan mode, it is determined whether any two events respectively set for the two segments neighboring each other across the aforementioned boundary have the same value specified as the value of the neutral loss, i.e. the difference between the mass-to-charge ratio selected by the first quadrupole mass filter 33 and the mass-to-charge ratio selected by the second quadrupole mass filter 36 (Step S9). If the common measurement mode has been identified as either the Q1 or Q3 scan mode, it is determined whether any two events respectively set for the two segments neighboring each other across the aforementioned boundary have the same values specified as the m/z values corresponding to the starting and ending points of the mass scan performed by either the first or second quadrupole mass filter 33 or 36 (Step S10).

In the case where the result of determination in any of Steps S4 through S9 is "No", there is no direct relation between the two partial chromatograms respectively created from the mass spectrometric data obtained at the two segments neighboring each other across the aforementioned boundary, and it is senseless to perform the chromatogram connection process. Accordingly, the operation proceeds to Step S12 to determine whether there is any boundary other than those for which the process of identifying the measurement mode has already been completed. If such a boundary still remains, the operation returns to Step 3 to once more perform the previously described processes for the two segments neighboring each other across that boundary. On the other hand, in Step S12, if it is determined that no such boundary remains, the operation proceeds to Step S13.

In the case where the result of determination in any of Steps S4-S6 is "Yes", the two partial chromatograms respectively created from the mass spectrometric data obtained at the two segments neighboring each other across the aforementioned boundary show a temporal change in the intensity of the same kind of ion. Accordingly, the process of connecting the partial chromatograms at that boundary is performed (Step S11). Specifically, as shown in FIG. 48, the two partial chromatograms are connected by linear interpolation between the two measurement points neighboring each other across the boundary (at time t2 in the present case), i.e. the last measurement point P1 in segment #1 and the first measurement point P2 in segment #2. Naturally, using a second or higher-order interpolation in place of the linear interpolation will create an even smoother connection of the two chromatograms.

If the result of determination in any of Steps S7-S9 is "Yes", the operation proceeds to the already described Step S10, where it is determined if any two events respectively set for the two segments neighboring each other across the aforementioned boundary have the same values specified as the m/z values corresponding to the starting and ending points of the mass scan performed by either the first or second quadrupole mass filter 33 or 36. If the result of determination in Step S10 is "No", the following process will be similar to the case where the result of determination is "No" in Steps S4-59; i.e. the operation proceeds to Step S12 to perform the previously described process. If the result of determination in Step S10 is "Yes", the following process will be similar to the case where the result of determination is "Yes" in any of Steps S4-S6; i.e. the operation proceeds to Step S11 to perform the previously described process.

If the result of determination in Step S2 or S12 is "No", there remains no boundary for which the chromatogram connection process needs to be performed. With a complete chromatogram thus obtained by connecting the partial chromatograms at the boundaries of the neighboring segments, it is now possible to perform various kinds of data processing, such as the detection of the starting and ending points of a peak, the detection of the location of the peak top and the calculation of the peak area, to obtain various kinds of information relating to that peak (Step S13). Then, the created chromatogram, accompanied by the calculated peak information, is presented to the operator on the screen of the display unit 8 (Step S14).

The aforementioned chromatogram connection process will be specifically described by means of the examples of FIGS. 3A and 3B. FIG. 3A shows one example of the event setting for three measurement modes primarily used for quantitative analyses in the GC/MS/MS of the present embodiment, and FIG. 3B shows the result of the chromatogram connection process in the present example.

In the case where the MRM mode with parameter values given as shown in FIG. 3A is set as the measurement modes for segments #1 and #2 neighboring each other across the boundary at time t2, the pair of m/z 300 as the mass-to-charge ratio of the precursor ion and m/z 200 as that of the product ion is present on both sides of the boundary. Although the event numbers are different, it is of no consequence since event numbers are not considered in the identification determination according to the present embodiment. Accordingly, a partial chromatogram based on the mass spectrometric data collected by a measurement according to event #1 of segment #1 and a partial chromatogram based on the mass spectrometric data collected by a measurement according to event #2 of segment #2 will be connected by linear interpolation in the previously described manner.

In the case where the Q1SIM mode with parameter values given as shown in FIG. 3A is set for segments #1 and #2 neighboring each other across the boundary at time t2, each of the two mass-to-charge ratios m/z 300 and m/z 200 is present on both sides of the boundary. Accordingly, the partial chromatogram based on the mass spectrometric data collected by a measurement according to event #2 of segment #1 and the partial chromatogram based on the mass spectrometric data collected by a measurement according to event #3 of segment #2 will be connected by linear interpolation in the previously described manner. Furthermore, the partial chromatogram based on the mass spectrometric data collected by a measurement according to event #3 of segment #1 and the partial chromatogram based on the mass spectrometric data collected by a measurement according to event #2 of segment #2 will be connected by linear interpolation in the previously described manner.

As described thus far, in the GC/MS/MS of the present embodiment, if the measurement modes specified in one or more events set for each segment and one or more parameter values corresponding to those modes are identical between two segments continuously located across a boundary, the partial chromatograms based on the mass spectrometric data collected in that measurement mode and under the measurement conditions specified by the aforementioned parameter values will be automatically connected, even if the event numbers are different. Therefore, even in the case where one chromatogram peak corresponding to one target compound lies across the boundary of two or more segments, it is possible to create a chromatogram with no missing portion at that boundary of the segments and provide correct peak information based on this chromatogram. This chromatogram can also be securely presented on the screen of the display unit 8.

Although the previously described embodiment was an example of applying the data-processing system for chromatographic mass spectrometry according to the present invention to a GC/MS/MS, it is evident that the present invention can also be applied to LC/MS/MS as well as GC/MS/MS. The present invention will exhibit particularly noticeable effects when applied to a chromatograph tandem quadrupole mass spectrometer, since this type of device has many measurement modes, and accordingly, allows the setting of complex contents in each event and a relatively large number of events for one segment. However, it is evident that the technique is also applicable to GC/MS or LC/MS using a quadrupole mass spectrometer with a single quadrupole mass filter.

It is evident that any change, modification or addition appropriately made in any other respect within the spirit of the present invention will naturally fall within the scope of claims of the present patent application.

EXPLANATION OF NUMERALS

1 . . . Gas Chromatograph (GC) Unit
10 . . . Sample Vaporization Chamber
11 . . . Micro Syringe
12 . . . Carrier-Gas Passage
13 . . . Column Oven
14 . . . Column
2 . . . Interface Unit
3 . . . Mass Spectrometer (MS) Unit
30 . . . Vacuum Chamber
31 . . . Ionization Chamber
32 . . . Ion Lens
33 . . . First Quadrupole Mass Filter
34 . . . Collision Cell
35 . . . Multi-Pole Ion Guide
36 . . . Second Quadrupole Mass Filter
37 . . . Ion Detector
38 . . . Analogue-to-Digital (A/D) Converter
4 . . . Data-Processing Unit
41 . . . Measurement Data Memory
42 . . . Measurement Condition Information Memory
43 . . . Chromatogram Creation Processor
5 . . . Analysis Controller
6 . . . Central Controller
7 . . . Input Unit
8 . . . Display Unit

The invention claimed is:

1. A data-processing system for chromatographic mass spectrometry for creating a chromatogram by processing data repeatedly collected by a chromatograph quadrupole mass spectrometer capable of setting a mass spectrometric measurement condition for each of segments corresponding to a plurality of time ranges continuously or discontinuously set on a time axis, comprising:
   a) a memory for storing a parameter value specified as a mass spectrometric measurement condition for each of the segments;
   b) a determiner for retrieving, from the memory, a predetermined parameter value for each of a pair of continuously located segments, and for determining whether the retrieved parameter values are identical; and
   c) a chromatogram creation processor for creating a chromatogram by connecting partial chromatograms based on the data collected for each of the aforementioned pair of segments under the corresponding measurement condition, when the determiner has determined that the retrieved parameter values are identical.

2. The data-processing system for chromatographic mass spectrometry according to claim 1, wherein:
   the memory holds a measurement mode and a parameter value specified as the mass-spectrometric measurement conditions for each of the segments;
   the determiner determines whether the measurement modes and the predetermined parameter values for the aforementioned two segments are identical; and
   the chromatogram creation processor connects the partial chromatograms if the measurement modes are identical and the parameter values are also identical.

3. The data-processing system for chromatographic mass spectrometry according to claim 1, further comprising a specifying section for allowing an operator to specify a mass-to-charge ratio, a range of mass-to-charge ratios or a target compound for which a chromatogram needs to be displayed, wherein:
   the determiner determines whether the displayed mass-to-charge ratios, ranges of mass-to-charge ratio or target compounds specified for the aforementioned two segments through the specifying section are identical as well as whether the predetermined parameter values corresponding to the aforementioned two segments are identical; and
   the chromatogram creation processor connects the partial chromatograms if the parameter values are identical and the displayed mass-to-charge ratios, ranges of mass-to-charge ratio or target compounds are also identical.

4. The data-processing system for chromatographic mass spectrometry according to claim 1, wherein:
   the chromatograph quadrupole mass spectrometer is a chromatograph tandem quadrupole mass spectrometer including a first quadrupole mass filter and a second quadrupole mass filter separated by a collision cell; and
   the aforementioned parameter value is a value of the mass-to-charge ratio of an on selected by one of the two quadrupole mass filters in one of the following modes:
   a Q1SIM mode, in which an ion is selected according to the mass-to-charge ratio thereof by the first quadrupole mass filter, while neither ion dissociation in the collision cell nor ion selection by the second quadrupole mass filter is performed; a Q3SIM mode, in which neither ion selection by the first quadrupole mass filter nor ion dissociation in the collision cell is performed, while an ion is selected according to the mass-to-charge ratio thereof by the second quadrupole mass filter; and an MRM mode, in which an ion is selected according to the mass-to-charge ratio thereof by the first quadrupole mass filter, the selected ion is dissociated in the collision cell, and a product ion created by dissociation is selected according to the mass-to-charge ratio thereof by the first and/or second quadrupole mass filter.

5. The data-processing system for chromatographic mass spectrometry according to claim 1, wherein:
the chromatograph quadrupole mass spectrometer is a chromatograph tandem quadrupole mass spectrometer including a first quadrupole mass filter and a second quadrupole mass filter separated by a collision cell; and
the aforementioned parameter value is a value of the mass-to-charge ratio of an ion to be selected by the second quadrupole mass filter in a precursor-ion scan mode.

6. The data-processing system for chromatographic mass spectrometry according to claim 1, wherein:
the chromatograph quadrupole mass spectrometer is a chromatograph tandem quadrupole mass spectrometer including a first quadrupole mass filter and a second quadrupole mass filter separated by a collision cell; and
the aforementioned parameter value is a value of the mass-to-charge ratio of an ion to be selected by the first quadrupole mass filter in a product-ion scan mode.

7. The data-processing system for chromatographic mass spectrometry according to claim 1, wherein:
the chromatograph quadrupole mass spectrometer is a chromatograph tandem quadrupole mass spectrometer including a first quadrupole mass filter and a second quadrupole mass filter separated by a collision cell; and
the aforementioned parameter value is a value of a neutral loss corresponding to the difference between the mass-to-charge ratio of an ion selected by the first quadrupole mass filter and the mass-to-charge ratio of an ion selected by the second quadrupole mass filter in a neutral-loss scan mode.

8. The data-processing system for chromatographic mass spectrometry according to claim 1, wherein:
the predetermined parameter value is a range of mass-to-charge ratios to be scanned in a measurement mode including a mass scan of a predetermined range of mass-to-charge ratios by a quadrupole mass spectrometer included in the chromatograph quadrupole mass spectrometer.

9. The data-processing system for chromatographic mass spectrometry according to claim 1, wherein:
the predetermined parameter value is the mass-to-charge ratio of a target ion in an SIM mode in which a measurement is performed for one mass-to-charge ratio or a plurality of mass-to-charge ratios sequentially selected in a quadrupole mass filter included in the chromatograph quadrupole mass spectrometer.

\* \* \* \* \*